United States Patent [19]
Toner et al.

[11] Patent Number: 6,127,177
[45] Date of Patent: Oct. 3, 2000

[54] CONTROLLED REVERSIBLE PORATION FOR PRESERVATION OF BIOLOGICAL MATERIALS

[75] Inventors: Mehmet Toner, Wellesley; Michael Russo, Wakefield; Robert Bieganski, Cambridge, all of Mass.

[73] Assignees: Massachusetts Institute of Technology; The General Hospital Corporation, both of Boston, Mass.

[21] Appl. No.: 09/151,821

[22] Filed: Sep. 11, 1998

[51] Int. Cl.$^7$ ............................... C12N 5/00; A01N 1/02
[52] U.S. Cl. .................................. 435/374; 435/1.3; 435/2
[58] Field of Search ................................ 435/374, 1.3, 2

[56] References Cited

U.S. PATENT DOCUMENTS

| | | | |
|---|---|---|---|
| 5,242,792 | 9/1993 | Rudolph et al. | 435/2 |
| 5,425,951 | 6/1995 | Goodrich, Jr. et al. | 424/520 |
| 5,595,866 | 1/1997 | Critser et al. | 435/2 |
| 5,648,206 | 7/1997 | Goodrich, Jr. et al. | 435/2 |
| 5,827,741 | 10/1998 | Beattie et al. | 435/374 |

FOREIGN PATENT DOCUMENTS

WO 97/45009  12/1997  WIPO.

OTHER PUBLICATIONS

Amato, I., Molecular Design Gets Into a Hole, Science 255:684, (1992).

Bayley, H., "Building Doors into Cells", Scientific American 62–67 (Sep. 1997).

Beattie, et al., "Trehalose: A Cryoprotectant That Enhances Recovery and Preserves Function of Human Pancreatic Islets After Long–Term Storage", Diabetes 46:519–523 (Mar. 1997).

Franks, et al., "Materials Science and the Production of Shelf–Stable Biologicals", BioPharm 39–42, 55 (1991).

Hildebrand, et al., "*Staphylococcus aureus* α–Toxin: Dual Mechanism of Binding to Target Cells", The Journal of Biological Chemistry 266(26):17195–17200 (1991).

McGann, et al., "Manifestations of Cell Damage After Freezing and Thawing", Cryobiology 25:178–185 (1988).

Russo, et al., "Reversible permeabilization of plasma membranes with an engineered switchable pore", Nature Biotechnology 15:278–282 (Mar. 1997).

Russo, M.J., "Controlled Poration of the Cell Membrane Using α–Toxin with a Metal–Actuated Switch", Master of Science Thesis in Mechanical Engineering at the Massachusetts Institute of Technology (1995).

Shalaev, E., "Changes in the Physical State of Model Mixtures during Freezing and Drying: Impact on Product Quality", Cryobiology 33:14–26 (1996).

Song, et al., "Structure of Staphylococcal α–Hemolysin, a Heptameric Transmembrane Pore", Science 274:1859–1866 (Dec. 13, 1998).

Spieles, et al., "An Attempt to Recover Viable Human Red Blood Cells After Freeze–Drying", Cryo–Letters 17:43–52 (1996).

Walker, et al., "An intermediate in the assembly of a pore–forming protein trapped with a genetically–engineered switch", Chemistry & Biology 2(2):99–105 (1995).

Walker, et al., "A pore–forming protein with a metal–actuated switch", Protein Engineering 7(3):655–662 (1994).

Russo, M. et al. "Controlled Poration of the Cell Membrane Using α–Toxin with a Metal–Activated Switch," Cryo '95; Society for Cryobiology, Jul. 6, 1995.

*Primary Examiner*—Sandra E. Saucier
*Assistant Examiner*—Vera Afremova
*Attorney, Agent, or Firm*—Nutter, McClennen & Fish, LLP

[57] ABSTRACT

A preservation method for biological material having cell membranes includes reversibly porating the cell membranes; loading a bio-protective agent having biopreservation properties to a predetermined intracellular concentration; preparing the bio-protective agent loaded biological material for storage; storing the biological material; recovering the stored biological material from storage; and reversing the cell membrane poration. H5 α-toxin, a genetically engineered mutant of *Staphylococcus aureus* α-hemolysin, may be used as a porating agent. Non-permeating sugars such as trehalose and sucrose may be used as the bio-protective agent.

13 Claims, 4 Drawing Sheets

SURVIVAL FOLLOWING FREEZE-THAW PROTOCOL
FOR VARYING CONCENTRATIONS OF TREHALOSE

— H5
□ WT

% SURVIVAL

EXTRACELLULAR TREHALOSE (M)

FIG. 4

POST HYDRATION RUSULTS AFTER
VACUUM DRYING

APPROXIMATE 3T3 CELL NUMBER PER WELL

PBS | 0.3M TREHALOSE | 0.3M SUCROSE

FIG. 5

CONTROLLED REVERSIBLE PORATION FOR PRESERVATION OF BIOLOGICAL MATERIALS

CROSS-REFERENCE TO RELATED APPLICATIONS

Not Applicable.

STATEMENT REGARDING FEDERALLY SPONSORED RESEARCH

This work was partially supported by NIH grants DK 46270 arid NS 26760.

FIELD OF THE INVENTION

The present invention relates to the preservation of biological tissue using reversible controlled poration methods to load intracellular protective agents to preserve cells by freezing and/or drying.

BACKGROUND OF THE INVENTION

With recent advances in cell transplantation, tissue engineering and genetic technologies, the living cell is becoming an important therapeutic tool in clinical medical care. From the use of living artificial skin and bone material to treat burn and trauma victims, to bioartificial devices and direct transplantation of cellular material to treat the increasingly long list of genetically-based diseases, living cells are increasingly incorporated into comprehensive treatment. In such a construct, the exogenous cells perform the multitude of complex tasks which the diseased tissue cannot. Successful long-term preservation and storage of mammalian cells is critical to the success of this type of medical care. Current preservation technology, including cryobiological technology, often requires rather complicated freezing and thawing protocols which may be specific for cell type, each requiring some variation of a cryopreservation agent (CPA) cocktail to help the cell overcome freezing stresses.

Most traditional cryopreservation protocols include the addition of 1.0–2.0 M of penetrating CPAs such as DMSO, glycerol, and ethylene glycol. Small carbohydrate sugars, such as trehalose, sucrose, and maltose have physicochemical properties (e.g., glass formation) for use as CPAs which are superior to traditional CPAs, however, mammalian cell membranes are not practically permeable to these materials.

In order to provide the preservation of mammalian cells necessary for application of living cells as a therapeutic tool in clinical medical care, new protocols for preserving living nucleated cells using low levels of non-toxic preservation agents and having simple procedures applicable to a variety of cells must be developed.

SUMMARY OF THE INVENTION

The present invention provides a method for preserving living cells that begins with the reversible poration of the cell membranes. In one preferred embodiment, this reversible poration is accomplished using H5 α-toxin, a genetically engineered mutant of *Staphylococcus aureus* α-toxin having five of its native residues replaced with histidines. Once porated, the biological material is loaded to a predetermined intracellular concentration with a bio-preservation agent such as a sugar having bio-preservation properties. The method of the invention may advantageously use low levels, less than or equal to about 1.0 M, of intracellular sugar and may use intracellular sugar alone as the protective agent, in combination with other intracellular sugars, or in combination with traditional penetrating CPAs.

The biological material is then prepared for storage. In general, the material may be prepared for storage by freezing and/or drying. In an exemplary embodiment, a simple plunge freezing technique is shown to have very high yield in the method of the invention. A vacuum drying protocol is also shown to result in post storage viability. In addition, air drying is well as freeze drying techniques may be employed.

Once the biological material is prepared for storage, it is stored in a manner appropriate to its preparation. Frozen material can be stored at cryogenic temperatures and dried material can dry stored at ambient or other temperatures as appropriate. Recovery of stored material is also appropriate to the method of its preparation for storage. Dried material can be rehydrated and frozen materials can be thawed. Cell membrane poration reversal may also be accomplished during the recovery step. When using H5 α-toxin, poration reversal may be accomplished by addition of $\mu M$ concentrations of $Zn^{2+}$ ions. This may be accomplished by placing the cells into a culture medium having a sufficient concentration of such ions.

BRIEF DESCRIPTION OF THE DRAWINGS

The invention will be more fully understood by reference to the following detailed description when considered in conjunction with the accompanying drawings, in which:

FIGS. 2A, C, E and G illustrate plating efficiency at 3 hours;

FIGS. 2B, D, F and G illustrate population survival and growth at 18 hours;

FIG. 4 shows the effects of trehalose concentration in the method of the invention on the survival rate for 3T3 fibroblasts plunge-frozen in liquid nitrogen and thawed at 37° C.; and FIG. 5 illustrates fibroblast viability after vacuum drying according to the method of the invention estimated by counting attached cells with characteristic spread morphology and the ability to grow and divide.

DETAILED DESCRIPTION OF THE INVENTION

Figure 1:
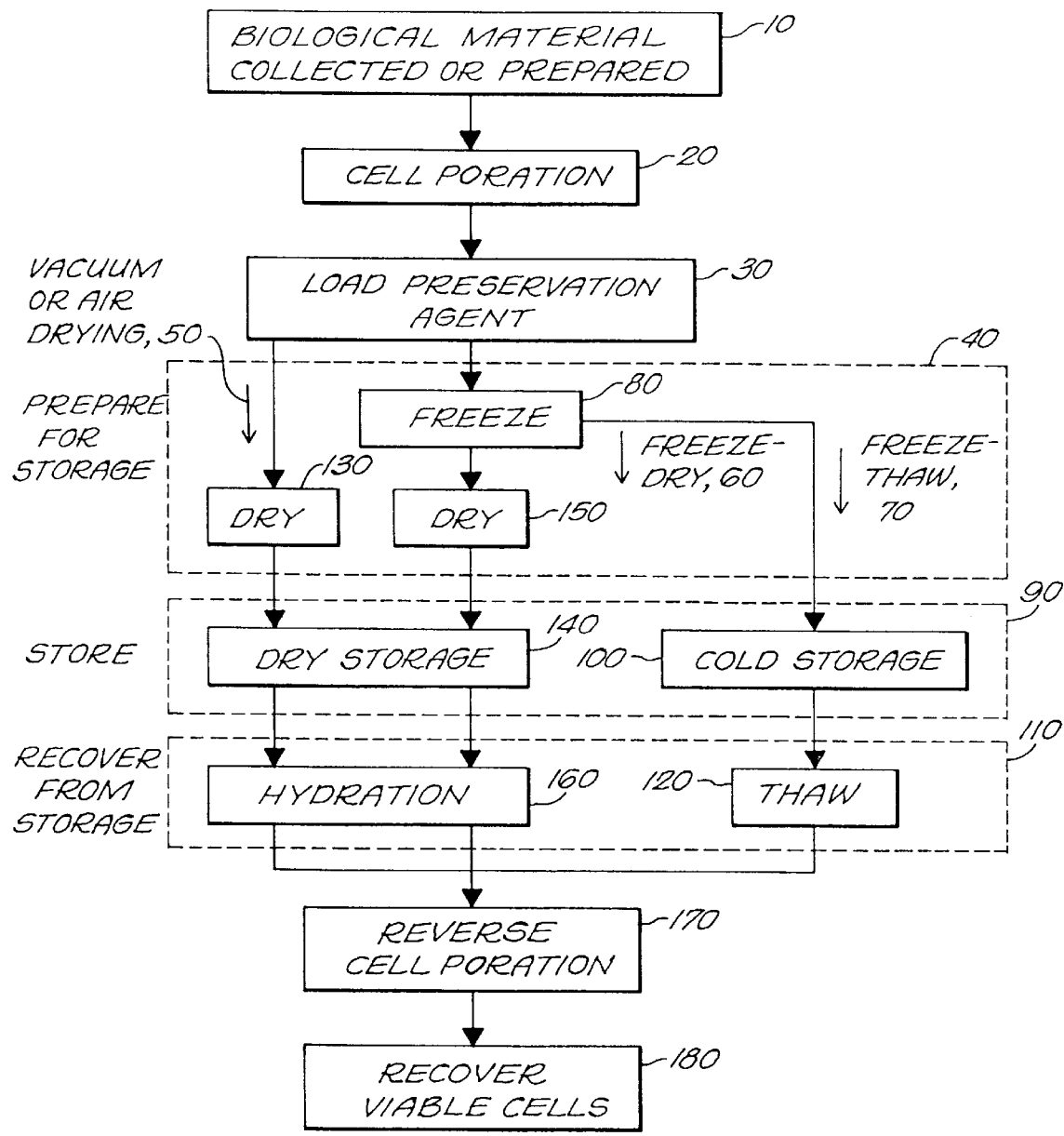
FIG. 1 is flow chart showing steps in the method of the invention.
Figure 2A:
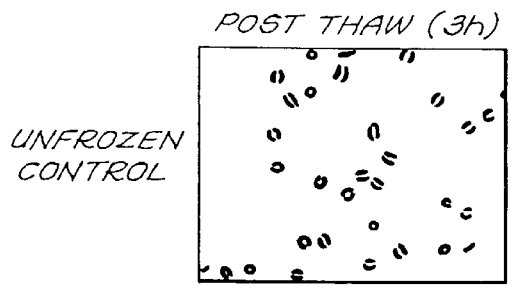
FIGS. 2A–G illustrate functional testing of cells loaded with 0.4M intracellular trehalose, plunge frozen in liquid nitrogen, and thawed at 37° C.
Figure 2B:
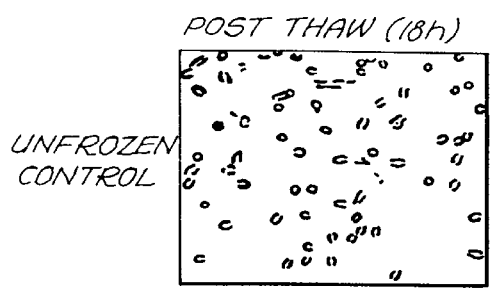
Figure 2C:
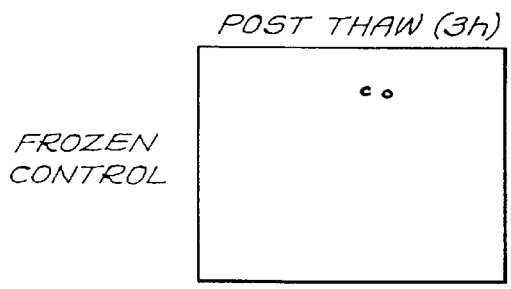
Figure 2D:
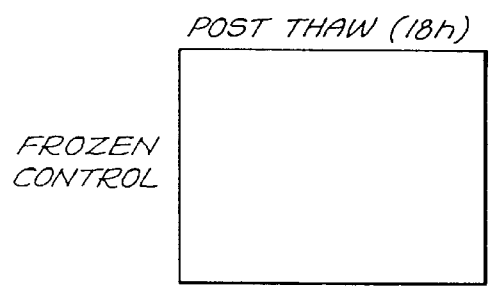
Figure 2E:
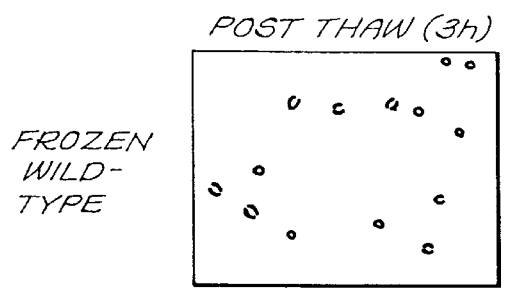
Figure 2F:
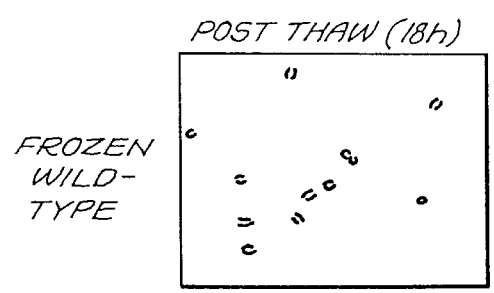
Figure 2G:
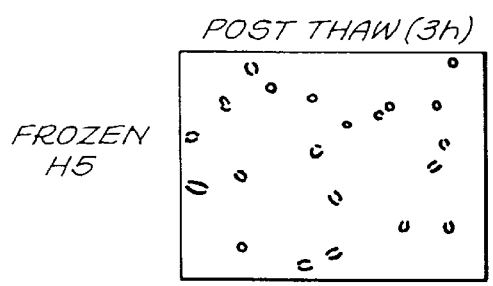
Figure 2H:
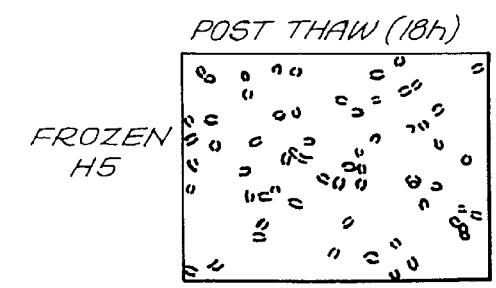

A method for preserving biological tissue of the invention, illustrated in FIG. 1, starts with the selection or isolation of the cells or tissue to be preserved 10. While the method of the invention may be used for the preservation of any biological material having lipid membranes, it is most useful for the preservation of living nucleated cells and, in particular, mammalian cells such as fibroblasts, hepatocytes, chondrocytes, keratinocytes, islets of Langerhans, granulocytes, and hematopoeitic cells including bone marrow cells, platelets, red blood cells and others.

The target cells are then porated or permeabilized 20 to facilitate the loading of a bio-preservation solution. Preferably, the target cells are reversibly porated, that is, pores are opened in the cell membranes of the target cells, but the poration process is controllably reversible as described herein. In one embodiment of the invention, the cell membranes are permeabilized by a genetically engineered mutant of Staphylococcus aureus α-toxin known as H5 (due to the replacement of five of its native residues with histidines). The structure of H5 is described in Song et al., "Structure of Staphylococcal α-hemolysin, a heptameric transmembrane pore," *Scienice*, 274, 1859–1866 (1996). H5, a 293 amino acid, 34 kDa protein forms uniform 2-nm homoheptameric transmembrane pores upon introduction into lipid bilayers. The amount of poration in the cell membranes is dose-dependent and the uptake of sugars through these pores is rapid. [Russo et al., "Reversible permeabilization of plasma membranes with an engineered switchable pore," *Nature Biotech*. 15, 278–282 (1997).]

Due to a targeted mutation, H5 pores are uniquely capable of being toggled between an open and closed state by the removal or addition of $\mu$M concentrations of $Zn^{2+}$ ions, respectively. [Walker et al., "A pore-forming protein with a metal-actuated switch," *Protein Eng*. 7, 655–662 (1994); Bayley, H., "Building doors into cells," *Sci. Am*. 277, 62–67 (1997).] The activity of the switch allows permeabilized cells to regain their original permeability and, as a result, maintain the viability and ultra-structural integrity.

Other poration agents may also be used with the method of the invention to reversibly porate target cells. Other variants of the Staphylococcus aureus α-toxin are available having different poration characteristics. In addition, under certain conditions it is possible to create reversible pores in cell membranes using wild type Staphylococcus aureus α-toxin (WT). WT may not be stable in all membranes when the cells are metabolically active (e.g., in a culture medium). As a result, for cells that can remain metabolically active for a longer period of time than the WT pores remain stable, the cells can shed even WT pores to reverse the poration effect. While some cells are too sensitive to survive for the required amount of time, other cells, such as 3T3 fibroblasts, may remain active in a porated state for up to 30 minutes and could be reversibly porated using WT.

Typically an H5 pore is about 2 nm in diameter. This size allows molecules having a molecular weight of up to about 1000 to enter the target cells through the H5 pores and permits many otherwise non-permeating bio-preservation agents to be used intracellularly. Other self-assembling membrane toxins capable of opening larger pores can be used or modified for use with the invention. While the application of larger pores may permit the use of larger molecules as intracellular bio-preservation agents, larger pores can have damaging effects on the target cell as well. For example, if the pores are large enough to admit the porating agent itself into the target cell, the porating agent may excessively permeabilize internal membranes and potentially cause irreparable damage to the target cell.

The target cells may be prepared for poration by trypsinizing, washing and suspending in a HEPES (N-[2-Hydroxyethyl]piperazine-N'-[2-ethanesulfonic acid]) Buffered Saline (HBS) solution. Preferably, all cell preparation should occur in HBS so that no antibodies against the poraling agents or proteolytic enzymes compromise the porating process. In order to porate the target cells, the HBS suspending solution should also contain a porating agent such as H5. As in the examples described below, the ratio of porating agent to target cell in the solution may be $2\times10^6$ cells/ml of the target cells to 25 $\mu$/ml of porating agent. The cells should be incubated in the porating agent containing solution for 10 minutes to allow for proper pore formation.

[Walker et al., "An intermediate in the assembly of a pore-forming protein trapped with a genetically engineered switch," *Chem. Biol*. 2, 99–105 (1995).] Of course, the precise amounts and times recited herein may be varied by a person of ordinary skill in the art in keeping with the invention where necessary to account for varying circumstances and desired effects. For example, some target cells may have receptors for H5 and may exhibit increased poration.

Following the permeabilization or poration step 20, a bio-preservation agent is loaded into the porated cell 30. The poration step of the invention allows otherwise non-permeating bio-preservation agents to be used intracellularly. As used herein, the term "non-permeating" refers to a compound that does not permeate the cell membrane of a mammalian cell under normal conditions in the necessary amounts in a reasonable amount of time (minutes to hours). These bio-preservation agents can include sugars as well as other non-permeating compounds either alone, mixed together, or in solution with other traditional bio-preservation agents. It is also possible that new bio-preservation agents will be synthesized specifically for intracellular application through pores of the type described herein.

Sugars having a stabilizing or preserving effect on biological material are especially useful in the present method. Exemplary sugars include trehalose, glucose, sucrose and maltose. Trehalose, a non-reducing disaccharide of glucose that is normally impermeant to mammalian cell membranes, is the most preferred sugar for use with the present method. It has an exceptional ability to stabilize and preserve proteins, viruses, and bacteria as well as an unusual ability to form stable glasses at high temperatures. Trehalose has physicochemical properties for use as a mammalian cell cryoprotective agent (CPA) that are far superior to traditional agents. Further, trehalose, contained in many food products, is relatively non-toxic and may allow for cryopreservation protocols which do not required CPA removal, resulting in an infusible end product. Sucrose, which has properties similar to those of trehalose and which is widely available and relatively inexpensive, may also be preferred for certain applications.

Sugar may be added to the cell suspension in an HBS solution to the final desired concentration. Porated cells may be incubated in the sugar containing solution for 45 minutes. A 45 minute interval has been demonstrated to be sufficient for the uptake of sucrose and trehalose for 3T3 fibroblast cells porated with 25 $\mu$/ml H5. Of course the length of time required for sugar uptake may vary with the type of cell and the level of cell poration. Sugar uptake may be measured by both the uptake of radiolableled sugar into porated cells as well as by the volumetric response of porated cells placed in a hypertonic sugar solution, yielding statistically correlative results.

Most traditional cryopreservation protocols include the addition of 1.0–2.0 M of penetrating cryoprotectants (CPAs) such as DMSO, glycerol, and ethylene glycol. However, using the method of the invention, small carbohydrate sugars such as trehalose, sucrose and maltose, to which mammalian cell membranes are not practically permeable, may be loaded to concentrations less than or equal to about 1.0 M, preferably less than or equal to about 0.4 M, and most preferably, the suspended, porated cells are loaded with about 0.2 M sugar.

In addition, reversible poration can improve the loading of conventional, permeating CPAs. Conventional CPAs used in conventional preservation procedures require tedious loading and removal steps. Typically, when a cell is exposed to a penetrating CPA such as DMSO, the cell initially shrinks because the permeability of the plasma membrane to water is significantly greater than its permeability to DMSO. Next, as the DMO slowly penetrates the membrane, the cell swells until equilibrium is achieved and loading of the CPA is complete. If the CPA is fully loaded in one step (e.g., 1–2 M DMSO), the initial cell shrinkage is fast and excessive, resulting in "osmotic" damage and cell death.

To prevent cell death, conventional CPAs are added in multiple steps. Typically, each step (depending, of course, on cell type) takes 15 to 45 minutes to load approximately 0.5 M CPA. The overall load process can thus take from 30 minutes to 2 hours or more. Similar circumstances occur during removal of the CPA from the cells. This long exposure to CPAs such as DMSO is "toxic" and can cause cell lysis. Applying conventional CPAs in the method of the invention using a reversible poration step increases the permeability to penetrating CPAs and accordingly lessens cell shrinkage and CPA loading times. As a result, the method of the invention can decrease both "osmotic" and "toxic" injuries, even using conventional CPAs.

It may also be beneficial to add certain high molecular weight bio-preservation agents that do not permeate through the pores. One such agent is raffinose. Raffinose attracts water that may diffuse into the biological material by forming a pentohydrate and stabilizes the glassy state against increases in moisture content (e.g. though cracked vials, etc.). Dextran of various molecular weights, having good glass formation properties, may be used extracellularly to allow increases in the storage temperature of a frozen stored sample. Other large molecules which do not permeate through H5 or similar pores may also be used extracellularly with the method of the invention to enhance the outcome of a particular preservation protocol.

Following the bio-preservation agent loading step 30, the biological material is prepared for storage 40. A variety of methods for freezing and/or drying may be employed to prepare the material for storage. In particular, three approaches are described herein: vacuum or air drying 50, freeze drying 60, and freeze-thaw 70 protocols. Drying processes have the advantage that the stabilized biological material may be transported and stored at ambient temperatures.

In contrast to current cryobiological technology which often requires complicated freezing and thawing protocols which may need to be specific to each type of cell being preserved, the method of the invention allows for a simple freeze-thaw protocol having a high survival rate, making cold storage a good choice as well. In the simple freezing step 80 of the invention, approximately 1 ml of cell suspension ($10^6$ cells/ml) may be placed into a cryovial, clipped into a cryovial holder, and plunged into liquid nitrogen ($LN_2$) for a sufficient time to bring the suspension to a cryopreservation temperature.

The suspended material can then be stored 90, 100 at cryopreservation temperatures, for example, by leaving the vials in $LN_2$, for the desired amount of time. The suspended material can then be recovered from storage 110 by thawing 120 in a 37° C. water bath with continuous, mild agitation for 5 minutes. For later analysis by the methods described below, thawed cells can diluted in Dulbecco's Modified Eagle Medium (DMEM) solution containing 10% bovine calf serum which has sufficient $Zn^{2+}$ to seal the H5 pores to reverse the cell poration 170 and promote cell recovery, or in any other appropriate dilution medium.

Protocols for vacuum or air drying 50 and for freeze drying 60 proteins are well characterized in the art [Franks et al., "Materials Science and the Production of Shelf-Stable Biologicals," *BioPharm*, October 1991, p. 39; Shalaev et al., "Changes in the Physical State of Model Mixtures during, Freezing and Drying: Impact on Product Quality," *Cryobiol.* 33, 14–26 (1996).] and such protocols may be used to prepare cell suspensions for storage with the method of the invention.

An evaporative vacuum drying protocol 130 useful with the method of the invention for preserving 3T3 murine fibroblasts may include placing 20 µl each into wells on 12 well plates and vacuum drying for 2 hours at ambient temperature. Of course, other drying methods could be used, including drying the biological material in vials.

Biological material prepared in this manner may be stored dry 140, and rehydrated by diluting in DMEM which contains serum (and sufficient $Zn^{2+}$ to seal the H5 pores) to reverse the cell poration 170 and promote cell recovery.

A method of the invention using freeze drying 60 to prepare the biological material for storage 40 begins with freezing 80 the cell suspension. While prior art freezing methods may be employed, the simple plunge freezing method described herein for the freeze-thaw method may also be used for the freezing step 80 in the freeze drying protocol.

After freezing, a two stage drying process 150 is typically employed. In the first stage, energy of sublimation is added to vaporize frozen water. When freeze drying biomaterials, the primary criterion for selecting the temperature of the primary drying phase is that it must be below the glass phase transition temperature of the freeze concentrated solution to avoid collapse and undesirable chemical reactions. In general, the highest possible temperature that will not damage the sample should be used so that sublimation will occur quickly. Typically, the primary drying occurs at a constant temperature maintained below the glass transition temperature for the freeze concentrated solution.

Secondary drying is performed after the pure crystalline ice in the sample has been sublimated. Secondary drying cannot take place unless the temperature is raised above the glass phase transition temperature of the freeze concentrated solute, however, it is crucial that sample temperature not rise above the collapse temperature above which the specimen is believed to mechanically collapse due to viscous flow.

Freeze dried materials can be stored 140, hydrated 160 and the cell poration reversed 170 in the same manner as described above for vacuum drying. Viable cells may then be recovered 180.

EXAMPLE 1

FREEZE-THAW PROCEDURE

CELL CULTURE

Examples were performed using NIH/3T3 murine fibroblasts (American type Culture Collection, Rockville, Md. cultured in Dulbecco's Modified Eagle Medium (DMEM; Life Technologies, Inc., Gaithersberg, Md. supplemented with 10% bovine calf serum (BCS, JRH Biosciences, Lenexa, Kans. and incubated at 37° C. with 10% $CO_2$ in air. At confluence, approximately every three days, cells were trypsinized in 0.1% trypsin solution (Life Technologies) and replated at a 40 fold reduction in cell number.

CELL PORATION

Fibroblasts in the log-phase of growth were trypsinized in 0.1% trypsin solution, washed twice in DMEM with BCS, and suspended ($2\times10^6$ cells/ml) in HEPES Buffered Saline (HBS:dH$_2$O 130 mM NaC1, 7.2 mM KC1, 20 mM HEPES (N-[2-Hydroxyethyl]piperazine-N'-[2-ethanesulfonic acid]); all Sigma, St. Louis, Mo. at a pH of 7.4. As indicated in Table 1 and FIG. 3, HBS suspending solution also contained either (i) 25 µg/ml of H5, the site-directed zinc-switchable mutant of *Staphylococcus aureus* (*S. aureus*) α-toxin (produced and purified as in Walker et al., "A pore-forming protein with a metal-actuated switch," *Protein Eng.* 7, 655–662 (1994)), (ii) 25 µg/ml of wild type *S. aureus* α-toxin (Sigma; WT), or (iii) no addition. Because of the variability among protein preparations, the hemolytic activities of the two porating proteins (H5 and WT) were equalized by measuring the release of hemoglobin from rat erythrocytes at OD 405 as adapted from Hildebrand et al., "*Staphylococcus aureus* α-toxin: Dual mechanism of binding to target cells," *J. Biol. Chem.* 266, 17195–17200 (1991). Though there was little difference in their activity (50% release of hemoglobin at 0.1 µg/ml after 3 hours of poration), the concentration of WT protein solution was slightly reduced so that its activity matched the activity of the 25 µg/ml of H5. Cells were incubated in the toxin containing solutions for 10 min to allow for proper pore formation.

SUGAR LOADING

Following poration, 0–1.0 M trehalose (final concentration) in HBS solution (Sigma) was added to the cell suspension, as indicated in FIG. 4. To allow for trehalose uptake, porated cells were incubated in the solution for 45 min. A 45 min interval has been demonstrated to be sufficient for the uptake of sucrose, a disaccharide similar to trehalose. [Russo et al., "Reversible permeabilization of plasma membranes with an engineered switchable pore," *Nature Biotech.* 15, 278–282 (1997).] This uptake was measured by both the uptake of radiolableled sugar into porated cells as well as by the volumetric response of porated cells placed in a hypertonic sugar solution, yielding statistically correlative results. By repeating the volumetric experiments using hypertonic trehalose solutions and 25 µg/ml of porating agent, volumetric equilibration over 90% over a 45 min interval was achieved, indicating, the equilibration of intracellular trehalose concentration with that of the suspending solution.

PRE-FREEZE EXPERIMENTS

Figure 3:
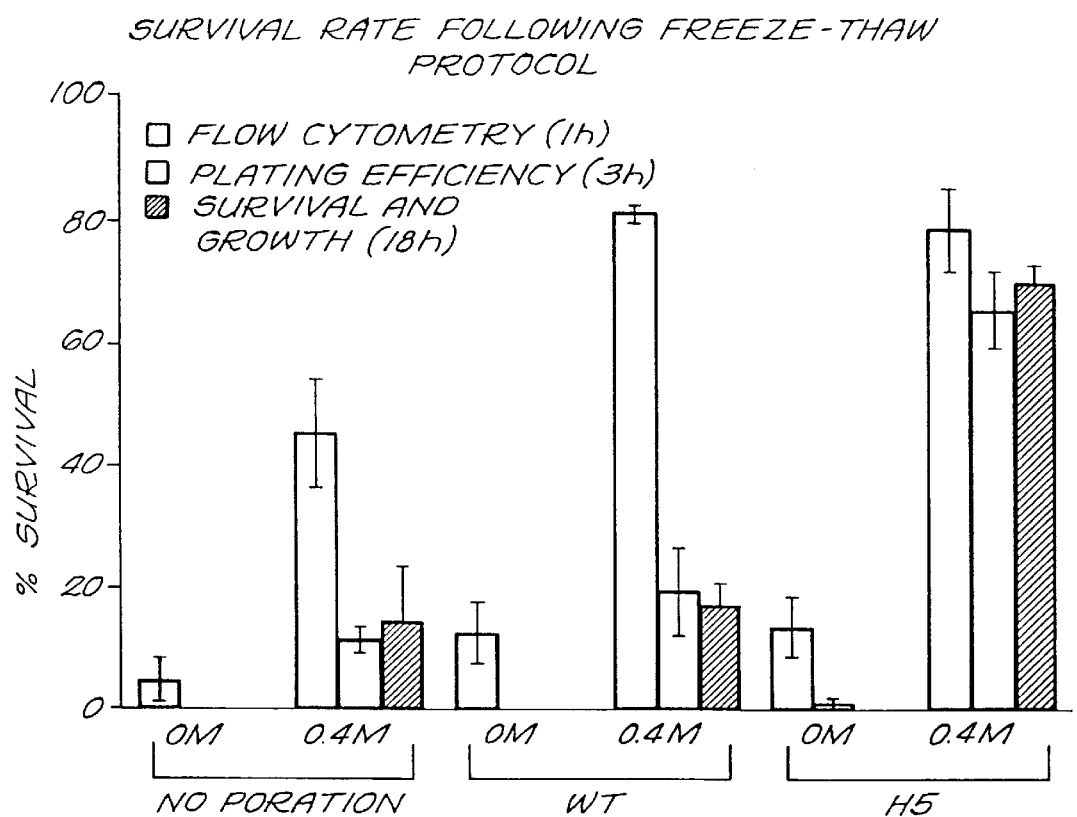
FIG. 3 illustrates the effects of trehalose in the method of the invention as an intracellular protective agent for 3T3 fibroblasts plunge-frozen in liquid nitrogen and thawed at 37° C.

As specified in Table 1 and FIG. 3, fibroblasts were treated with varying poration and trehalose schemes by the methods described above. To determine the effects of these pre-freeze treatments on cell viability and function, cells were then assayed by flow cytometric analysis and by measuring cellular plating efficiency, clone forming ability, and population growth as described below.

CRYOPRESERVATION PROTOCOL

Following a variety of poration and trehalose treatments as indicated in FIGS. 3 and 4, 0.9 ml of the cell suspension ($10^6$ cells/ml) was placed into a 1.9 ml cryovial (Nalgene, Rochester, N.Y.), clipped into a cryovial holder (TS Scientific, Perkaise, Pa.), and plunged into liquid nitrogen (LN$_2$) and stored there for 60 minutes. Individual vials were then thawed in a 37° C. water bath with continuous, mild agitation for 5 min. For later analysis by the methods described below, thawed cells were diluted in serum containing DMEM which contained sufficient Zn$^{2+}$ to seal the H5 pores and promote cell recovery.

FLOW CYTOMETRY

At 15 minutes, 1 hour, and 2 hours following either the pre-freeze cell preparation (poration and trehalose loading) or after the freeze-thaw protocol, two fluorescent dyes, calcein (5 µM; Molecular Probes; Dugene Oreg.) and ethidium homodimer (EH; 10 µM; Molecular Probes) were added to HBS cell suspensions to assess viability of the cells. Calcein fluoresces green (510 nm) when retained intracellularly and indicates a live cell with an intact cell membrane, while EH fluoresces red (617 nm) when bound to DNA and thus stains the nucleus of a dead cell. Following calibration, cells were run at low flow rates through the Beckton Dickinson FACSCalibur flow cytometer (San Jose, Calif.) to measure forward and side scatter as well as take emission readings at 530±30 nm and 63±022 nm of 10,000 particles. Cells, as indicated by size and ganularity, were evaluated for their emissions at the two wavelengths indicated above. High green and low red fluorescence was scored as live, while low green and high red were scored as dead; those displaying low or high values for both were scored as dead. Since the live/dead data is delivered as a percentage, total cell yield was determined by counting on a hemocytometer (Baxter, McGaw Park, Ill.). Those which do not appear in the total yield, presumably cells which have lysed and dispersed, less those lost by cell handling and transfer as determined by control experiments, were likewise scored as dead.

PLATING EFFICIENCY

Following either the pre-freeze cell preparation or after the freeze-thaw protocol, each cell suspension was diluted in 12 ml DMEM with BCS and plated in a P75 tissue culture flask (Falcon, Franlin Lakes, N.J.). After three hours, flasks were washed twice with HBS and those cells remaining in the flask were trypsinized and counted using a hemocytometer. For pre-freeze experiments, reported values are the number of cells which were successfully plated normalized to the total number of cells input to the system following preliminary cell handling. For freeze-thaw conditions, reported values; are the number of cells which successfully plated normalized to the total number of cells input to the system following preliminary cell handling and any toxin treatment. Micrograph images were obtained on a Nikon Diaphot microscope (Nikon Ph2, NA-.4; Tokyo, Japan) at 120x magnification and captured with Metamorph imaging software and are shown in FIGS. 2A–G.

CLONOGENIC ASSAY

For each condition, approximately 200 of the cells that had plated in 3 hours were replated in a P75 for one week. To obtain 200 fibroblast, cells were diluted to $2\times10^5$ cells/ml, and 1 µl of cell solution was introduced into a P60 petri dish (Falcon) containing 12 ml of DMEM with BCS. After one week, cells were fixed by a 0.5% glutaraldehyde wash and stained by Rhodamine B (Sigma) to enhance colony visibility. The number of colonies formed was determined by visual inspection.

SURVIVAL AND GROWTH

Following either the pre-freeze cell preparation or after the freeze-thaw protocol, the cell suspensions for each condition were diluted in 12 ral of DMEM with BCS and plated in P75 flasks. After 18 hours, approximately two population doubling cycles, flasks were washed twice with HBS. Fibroblast populations were then trypsinized and counted on a hemocytometer. For pre-freeze measurements, data was normalized to the unporated control case with no trehalose addition. For post-thaw experiments, reported values are the total number of cells in each flask normalized to an unfrozen control population otherwise treated identically to the experimental condition.

STATISTICAL ANALYSIS

Data were analyzed by ANOVA factorial and evaluated with Fisher's Post-Hoc Test for at least 97% confidence ($p \leq 0.03$). Pre-freeze flow cytometry, plating efficiency, and clonogenic experiments were repeated at least twice, and 18 hours growth experiments were repeated at least three times. For all experiments, at least two independent measurements were performed. Data reported are normalized averages of total viable and functional cell populations at indicated time points±the standard error of the mean (SEM).

EXAMPLE 2

VACUUM OR AIR DRYING PROCEDURE

The efficacy of intracellular trehalose for vacuum dried fibroblasts was also tested. NIH/3T3 murine fibroblasts, prepared as in Example 1, were resuspended in phosphate buffered saline (PBS) solution and the cell density was counted. Cell density was then adjusted to 100,000 cells/ml by diluting with PBS and the sample was divided into three equal aliquots of 4.0 ml each. To each aliquot, 1.0 ml of 25 $\mu$g/ml H5 was added, reducing cell density to $8\times10^4$. The aliquots were incubated at room temperature for 15 minutes with occasional mixing.

In the first two aliquots, enough 1.0M stock solution of either trehalose or sucrose in PBS was added to obtain a final sugar concentration of 0.3M. In the third aliquot, an equivalent amount of PBS, without sugar, was added.

The three aliquots were dispersed in triplicate wells at 20 $\mu$l/well into four duplicate 12-well plates. Two of the twelve well plates were incubated at 37° C. and 10% $CO_2$ as controls. The remaining two plates were vacuum dried for 2 hours at ambient temperature. After drying, the dried samples were rehydrated and the poration reversed with serum containing DMEM.

Viability assays were performed by counting attached cells at 3 hours, and cells that remained attached and divided during the next 24 hours. The experiments were repeated three times. As shown in FIG. 5, an average of 48±3 cells that successfully attached at three hours for the trehalose sample, and 36±3 for the sucrose sample. Adjusting for cell loss due to handling, poration, etc. using the control samples, survival rates of 4% for the cells dried in trehalose and 3% for the cells dried in sucrose were obtained. Periodic microscopic examination of the attached cells over the next 24 hours indicated that the attached cells were able to maintain the characteristic spread morphology and undergo proliferation.

RESULTS

The examples demonstrate that 0.2 M of intracellular trehalose alone is sufficient to provide protection for over 80% of the 3T3 fibroblasts cryopreserved in a simple liquid nitrogen plunge protocol. This concentration is five-fold to an order of magnitude lower than the functional concentrations of traditional CPAs such as $Me_2SO$ and ethylene glycol. Further, this protocol allowed for the preservation of 1 ml samples, and did not have a CPA removal requirement. Based on these results, the method of the invention allows a simple cryopreservation protocol for mammalian cells.

To illustrate this point, a variety of assays were implemented to evaluate the condition of the cells at various time points following the uptake of trehalose as well as after the freeze-thaw cycle. At early time points, 15 and 60 min after treatment, cell viability was evaluated by assaying the integrity of the cell membrane with a double-label fluorescent stain. Next, after three hours in culture, we tested the normal ability of these cells to attach to the polystyrene substrate and spread, taking on an elongated spindle-like shape. Finally, cells which attach should then secrete extracellular matrix and undertake the complex task of cell division. Because it involve, a complex series of steps involving DNA replication, spindle formation, and protein synthesis, mitosis is an ideal marker for the functional integrity of fibroblasts. Thus, incorporating both the death of cells as well as the ability of surviving cells to divide, the population's growth over 18 hours is indicative of the overall freezing damage suffered by the cells.

As a baseline for the freezing results, the condition of cells following poration and exposure to trehalose was evaluated. Overall, these data for 18 hours growth indicate that over 95 % of fibroblasts can withstand the osmotic shock of being placed into 0–0.4 M trehalose, with porated cells suffering only an additional 10% loss. Since fibroblasts reach their minimum volume when exposed to about 0.4 M trehalose (data not shown), the excessive dehydration and osmotic forces caused by concentrations higher than this threshold are most likely responsible for their loss of viability. Porated cells do not shrink to the same degree as non-permeabilized cells due to the altered water and solute transport properties of permeabilized cell membranes. They, therefore, seem to withstand the osmotic insult more readily. Moreover, the engineered H5 switch, in combination with this osmotic advantage, causes the H5 treated cells to outperform both other conditions by 20–50% for much of the upper range of trehalose concentrations. Based on these and previous data, trehalose loading was targeted at 0–0.4 M for the design of freezing protocols. This range is comparable to the trehalose concentrations used for protein and virus preservation. Since trehalose is non-toxic at these concentrations, freezing protocols were designed without a CPA removal step.

EFFECT OF PORATION AND TREHALOSE CONCENTRATION ON NON-FROZEN SAMPLES

To maximize the final post-thaw survival of the samples, the pre-freeze treatment steps were optimized, finding conditions for permeabilization and trehalose loading which were minimally damaging to cells. Pre-freeze control experiments were performed under a variety of permeabilization and trehalose conditions to measure the amount of cell loss attributable to each stage of treatment. Overall, large numbers of fibroblasts, over 85%, maintained viability and function following permeabilization by either WT or H5 either with or without trehalose addition. The complete set of pre-freeze control data is reported in Table 1. These data were normalized to cell populations following a 4% loss resulting from cell handling (pipetting, centrifugation, etc.) as measured by hemocytometer.

TABLE 1

Evaluation of Pre-freeze and Post Thaw Cells Porated and Loaded with Trehalose

| H5/WT | 0.4M Trehalose | Flow Cytometry (1 h) | Plating Efficiency (3 h) | Survival and Growth (18 h) |
| --- | --- | --- | --- | --- |
| Pre-Freeze Conditions | | | | |
| — | - | 94.5 ± 3.3 | 91.5 ± 1.5 | 100 |
| — | + | | | 98.4 ± 2.6 |
| WT | - | 95.0 ± 1.0 | 92.2 ± 1.8 | 90.0 ± 3.6 |
| WT | + | 78.0 ± 3.0 | 80.0 ± 3.0 | 87.4 ± 0.9 |
| H5 | - | 91.9 ± 4.6 | 87.5 ± 5.6 | 91.5 ± 3.9 |
| H5 | + | 85.1 ± 3.1 | | 84.2 ± 5.8 |
| Post-Thaw Conditions | | | | |
| — | - | 4.5 ± 3.5 | 0.0 ± 0.0 | 0.0 ± 0.0 |
| — | + | 45.0 ± 8.8 | 11.2 ± 2.1 | 14.2 ± 8.9 |
| WT | - | 12.1 ± 4.9 | 0.0 ± 0.0 | 0.0 ± 0.0 |

TABLE 1-continued

Evaluation of Pre-freeze and Post Thaw Cells Porated and Loaded with Trehalose

| H5/WT | 0.4M Trehalose | Flow Cytometry (1 h) | Plating Efficiency (3 h) | Survival and Growth (18 h) |
|---|---|---|---|---|
| WT | + | 81.3 ± 1.2 | 19.3 ± 7.3 | 16.9 ± 3.6 |
| H5 | − | 13.2 ± 4.9 | 0.8 ± 0.8 | 0.0 ± 0.0 |
| H5 | + | 79.0 ± 6.4 | 66.1 ± 6.3 | 70.8 ± 2.1 |

Specific experiments were performed to evaluate the effect of simply suspending cells in HBS as would occur during the loading of trehalose. Flow cytometric analysis with live/dead stain indicated that 3.0±0.4% of the cell population was not viable following a two hour of exposure to HBS. At three hours, cells suspended in DMEM with serum plated and spread effectively with no additional losses. Finally, by 18 hours, the cell populations increased by a factor of 2.25, indicating a baseline for normal cell growth and population doubling dynamics. Similarly, the survival and growth of non-porated cells suspended in 0.4M trehalose in HBS (98.4±2.6) was not statistically different from that of the population suspended in HBS alone (p=0.777).

To better understand the consequences of the trehalose loading protocol, the effect of poration and trehalose treatment on the viability and function of unfrozen fibroblasts was quantified by evaluating the condition of cells porated with 25 µg/ml of a porating agent, either alone or with 0.4 M trehalose by a battery of assays as shown in Table 1. Interestingly, none of the porated conditions was significantly different from any other porated condition regardless of porating agent (i.e. WT vs. H5) and independent of the addition of trehalose (p<0.0300 for all comparisons). Therefore, it appears that we can load 0.4 M trehalose into fibroblasts with minimal loss to the cell population. In addition, for all conditions tested, cells which were able to attach and spread at 3h were also able to form colonies after one week of culture.

In developing the freezing protocol, the effect of trehalose concentration on the survival of either unporated cells or cells porated with H5 or WT was measured. As reported in Table 2, cells exposed to trehalose did not demonstrate a significant loss of viability of function for concentrations less than 0.4 M independent of poration (p>0.5000 for all comparisons). At 0.6 M, H5 porated cells demonstrated 80% survival, thereby outperforming the WT and unporated conditions by over 20% (p=0.0010 and 0.0065, respectively). Finally, from 0.8 to 1M, H5 and WT treated populations suffer loss of half of their populations, while unporated cells retained only 10% viability. From this study, it appears that fibroblasts should preferably be exposed to less than or equal to about 0.4 M trehalose in order to maintain high viability.

TABLE 2

Survival of Pre-Freeze Cells: Dose Response of Trehalose

| Trehalose (M) | No Poration | WT | H5 |
|---|---|---|---|
| 0.0 | 100 | 90.0 ± 3.6 | 91.5 ± 2.2 |
| 0.2 | 99.2 ± 3.3 | 95.6 ± 7.0 | 98.1 ± 6.4 |
| 0.4 | 98.5 ± 2.6 | 87.4 ± 0.9 | 84.1 ± 3.3 |
| 0.6 | 60.7 ± 3.3 | 52.3 ± 3.2 | 79.1 ± 3.0 |
| 0.8 | 39.4 ± 1.0 | 59.5 ± 4.4 | 52.0 ± 0.9 |
| 1.0 | 9.1 ± 1.6 | 44.5 ± 2.3 | 60.6 ± 2.6 |

EFFECT OF PERMEABILIZATION AND INTRACELLULAR TREHALOSE ON PLUNGE-FROZEN CELLS

The use of trehalose as an intracellular cryoprotectant was demonstrated by testing the survival and function of cells treated with 25 µg/ml of H5 and 0.4 M trehalose, subsequently plunged in $LN_2$, and finally thawed in a 37° C. water bath. The results demonstrate the effectiveness of trehalose as an intracellular CPA and illustrate the importance of the H5 switch. They are qualitatively outlined in the micrographs of FIG. 2. The first two panels (A, B) show unfrozen and untreated control samples at 3 and 18 hours after plating. Large numbers of cells attach, spread, assume the spindle shape of fibroblasts, and subsequently divide. This is in sharp contrast to the frozen and untreated case (C, D) in which all cells die as a result of the freeze-thaw process. Interestingly, though a moderate fraction of cells treated with WT and loaded with trehalose appear to survive the freeze-thaw protocol (E), these cells are neither able to sustain their viability nor divide properly, resulting in very small populations at 18 hours (F). On the other hand, H5 porated cells loaded with trehalose demonstrate a substantial amount of survival and high plating efficiency (G), as well as a normal degree of cell division resulting in large populations at 18 hours (H).

These data, as well as cell viability at 1 hour, 3 hours and 18 hours, were quantified as shown in FIG. 3. Again, these data demonstrate the consistently high viability and function of cells treated with intracellular trehalose loaded through H5 pores, as compared to all control conditions. For the H5 and trehalose samples, at 1 hour post-thaw, live/dead staining measured 79.0±6.4% viable cells. At three hours, 66.1±6.4% cells plated and spread with 211.6±5.2 colonies formed from approximately 200±12 of these functional cells. At 18 hours, the cells formed populations which were 70.8±2.1% of the size of control populations which were likewise treated with H5 and trehalose but which were not frozen (Table 1). Moreover, these data show no significant difference among time points, implying that cells which were alive at 1h continued to be viable and functioning (p>0.1000 for all comparisons). In addition, these data are 70–80% higher than all control data to which trehalose was not added (p<0.0001). Further, though at 1 hour the H5 and WT (81.3±1.2%) conditions treated with trehalose are not statistically different (p=0.8073), the loss of over 60% of the WT condition's population at 3h (19.3±7.3%) and 18 hours (16.9±3.6%), resulted in a large and statistically significant difference between the use of WT and. H5 as the porating agent (p<0.0001). In fact, WT porated cells loaded with trehalose performed so poorly, that their survival was not statistically different from the case in which trehalose was simply acting extracellularly (p>0.4000). Though non-frozen samples previously indicated little difference between WT and H5 treatment, these post-thaw data indicate a dramatic difference, implying that the engineered H5 is the preferred porating agent for loading trehalose into cells prior the freezing.

EFFECT OF TREHALOSE CONCENTRATION OF PLUNGE-FROZEN CELLS

Since the use of any intracellular CPA requires a balancing between the added freezing protection afforded by higher concentrations and losses due to excessive osmotic forces and toxicity, the effect of trehalose concentration on H5 porated cell survival and growth at 18 hours was measured. These data, as illustrated in FIG. 3, indicated an inverted U-shaped curve, with 0.2 M treated cells performing remarkably well with an 18 hour population of 79.2±4.0%. At 0.1 M the population was significantly lower at 28.6±3.4% (p<0.0001) while at higher concentrations the population size steadily decreased, remaining statistically significant from the 0.2 M condition (p<0.0010). As the concentration increases, the curve flattens which leads to statistically insignificant (p=0.9477) differences between 0.6 M (28.5±2.3%) and 0.8 M (29.4±2.1%). Overall, these data imply that for a freezing protocol with a one step trehalose loading process, 0.2 M is the preferred concentration, providing over 80% survival and function with 3T3 fibroblasts.

EFFICACY OF INTRACELLULAR SUGARS FOR VACUUM DRYING OF CELLS

Fibroblasts were also porated with H5 and loaded with 0.3 M trehalose or sucrose in order to test the efficacy of the preservation method for dried as well as frozen cells. One group of cells was porated with H5 but loaded with PBS only with no sugar for use as a control. Adjusting for cell loss due to handling, poration, etc. using the controls, survival rates of 4% for cells dried in trehalose and 3 % for cells dried in sucrose were obtained using a simple ambient temperature vacuum drying step. Periodic microscopic examination of the attached cells over 24 hours indicated that the attached cells were able to maintain the characteristic speed morphology and undergo proliferation. Both trehalose and sucrose were thus shown to be effective in protecting cells subjected to vacuum drying.

CONCLUSIONS

The freezing experiments demonstrate that cells permeabilized with H5 and loaded with less than or equal to about 0.4 M trehalose have a dramatically higher level of viability and function as compared to all other tested conditions. In fact, all controls without trehalose resulted in 100% mortality, while the H5 and trehalose combination resulted in over 70% survival and growth. The presence of trehalose as well as the reversible permeabilization afforded by H5 has multiple advantageous effect, which may bolster cell survival. Primarily, intracellular trehalose, by increasing cytosolic viscosity, may inhibit the growth of intracellular ice crystals, thus mitigating cell damage. Further, as has been demonstrated for isolated biomaterials, trehalose may stabilize cell membranes and proteins during freezing, thereby preventing membrane leakiness and favoring native protein configuration. Likewise, sample stability may be improved by trehalose's ability to permit a higher temperature glass transition in the unfrozen fraction.

Though both the H5 and WT conditions have presumably similar intracellular trehalose contents, the H5 condition demonstrated 56% higher survival and growth. This result underscores the advantage of the zinc-actuated switch. Since DMEM with serum (post-thaw medium) contains $\mu$M concentrations of $Zn^{2+}$ ions, the H5 pores are blocked under these post-thaw conditions. Thus, the cells treated with the engineered and switchable H5 molecules and subsequently plated in DMEM with serum regain their natural permeability to small molecules, permitting a return to normal homeostasis and subsequent recovery. Without the benefit of the resealing, WT permeabilized cells cannot recover properly post-thaw, and they ultimately die. As suggested above, under certain limited circumstances it may be possible to reversibly permeabilize target cells with WT where the WT pores are unstable and are shed by the cells before the cells die off from the permeabilization effects.

Although the initial freezing experiments used 0.4 M trehalose, the maximum concentration indicated by pre-freeze evaluation, the effect of varying the trehalose concentration on the post-thaw survival of H5-permeabilized cells was evaluated by varying the trehalose dose up to 1.0 M. The resulting trehalose dose response is represented by an inverted U-shaped curve with a maximal survival of over 80%, at 0.2 M. Apparently, below 0.2 M there is not adequate trehalose present to afford proper protection. Above this, the loss of viability seems to be a direct result of exposing the cells to excessive osmotic pressure during loading and of not removing the trehalose after thawing.

To probe the mechanism of trehalose protection and test whether intracellular ice formation occurs under the exemplary conditions, the temperature excursion of plunge-frozen H5 and trehalose treated samples was measured with a thermocouple, and the measured cooling rates reproduced on a cryomicroscope. Fairly independent of position, plunged cells experienced a cooling rate of $-70°$ C./min from 22° C. to $-15°$ C., and $-160°$ C./min to $-175°$ C. with a latent heat release at $-12$ to $-15°$ C. When fibroblasts treated with H5 and loaded with trehalose were deliberately exposed to this cooling protocol on a cryomicroscope, cells darkened following the seeding of extracellular ice, including that intracellular ice had formed. If this indeed reflects what occurs in the cryovial, the trehalose must somehow protect the cell from the damaging effects of intracellular ice formation.

Often, preservation protocols have been evaluated at times shortly following thaw, resulting in the presumption of success. The data presented here demonstrates that such testing is not a reliable indicator of a protocol's effectiveness. For the plunge freeze experiments, the earliest fluorescent tests for cell viability are not indicative of the final condition of cell populations. At 15 minutes, all frozen conditions, except untreated controls, demonstrate 60–80% viability. However, after one hour cells treated only with either H5 or WT retain 10% viability, and cells with trehalose added alone have 45% viability. Only cells treated with both a porating agent and trehalose retain 70–80% viability and function after 1 hour. Further, as indicated by plating at 3 hours and growth at 18 hours, the H5 and trehalose condition leads to long term cell survival and function. These data imply that damage due to freezing stresses, at least in part, does not result in the immediate destruction of cells, but rather in a gradual loss of viability.

The Examples show the successful cryopreservation of 3T3 murine fibroblasts using less than or equal to 0.4 M trehalose as the sole CPA in a rather simple $LN_2$ plunge cryopreservation protocol. The trehalose concentration used is an order of magnitude lower than what is required for mammalian cells in traditional constructs utilizing traditional CPAs. Survival, however, is dependent on the reversible permeabilization afforded by the H5 switchable pore. Further, freezing and thawing took place in a rather large sample volume (~1 ml) and without any regard for the cooling profile, seeding temperature, or plunge temperature. This suggests that the use of small carbohydrates introduced intracellularly can allow the preservation of living material using low concentrations of CPA, thus avoiding toxicity effects, and implementing simplified freezing protocols.

The efficacy of intracellular trehalose was also shown for vacuum dried fibroblasts. Vacuum drying at ambient temperature of reversibly porated fibroblasts loaded with trehalose or sucrose resulted in viable cells after rehydration.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A method for dry storing living nucleated mammalian cells having cell membranes, comprising:
   a. Applying a membrane toxin to reversibly porate the cell membranes of the nucleated cells;
   b. Loading an agent having bio-preservation properties to a predetermined intracellular concentration sufficient for preserving the cellular material, the predetermined intracellular concentration being less than or equal to about 1.0 M, the bio-preservation agent comprising a sugar;
   c. Drying the sugar loaded cells to a level sufficient to permit dry storage;
   d. Placing the dried cells in dry storage;
   e. Rehydrating the dried cells to a level sufficient for cell viability; and
   f. Reversing the cell membrane poration to an extent sufficient to permit survival and growth of the cells;
   wherein sugar is the only bio-protective agent employed.

2. The method of claim 1, wherein the cell membranes are reversibly porated using H5 α-toxin.

3. The method of claim 1, wherein the sugar having bio-preservation properties is selected from a group consisting of trehalose, sucrose, glucose and maltose.

4. The method of claim 3, wherein the membrane toxin forms pores of at least about 2.0 nanometers in the membrane.

5. The method of claim 3, wherein the biological material is loaded with an intracellular concentration of sugar less than or equal to about 0.4 M.

6. The method of claim 3, wherein the drying is accomplished by freeze drying.

7. The method of claim 6, wherein the sugar loaded cells are plunge frozen to a cryogenic temperature.

8. The method of claim 3, wherein the drying is a vacuum or air drying.

9. The method of claim 8, wherein the drying is performed at a non-cryogenic temperature.

10. A method for cryopreserved living nucleated mammalian cells having cell membranes, consisting essentially of:
    a. Applying a membrane toxin to reversibly porate the cell membranes of the nucleated cells using H5 α-toxin;
    b. Loading the porated cells with a bio-preservation agent consisting essentially of a sugar to a predetermined intracellular concentration sufficient for preserving the nucleated cells, the predetermined intracellular concentration being less than or equal to about 1.0 M;
    c. Freezing the sugar loaded cells to a cryopreservation temperature;
    d. Storing the frozen biological material at a cryo-storage temperature;
    e. Thawing the cryo-stored biological material to a viable state; and
    f. Reversing the cell membrane poration to an extent sufficient to permit survival and growth of the cells.

11. The method of claim 10, wherein the sugar having bio-preservation properties is selected from a group consisting of trehalose, sucrose, glucose and maltose.

12. The method of claim 11, wherein the intracellular concentration of the sugar is less than or equal to about 0.4 M.

13. The method of claim 11, wherein the cells are plunge frozen.

* * * * *